United States Patent
Tyber et al.

(10) Patent No.: US 9,615,870 B2
(45) Date of Patent: *Apr. 11, 2017

(54) INTRAMEDULLARY FIXATION ASSEMBLY AND METHOD OF USE

(71) Applicant: Extremity Medical, LLC, Parsippany, NJ (US)

(72) Inventors: Jeff Tyber, Landing, NJ (US); Jamy Gannoe, West Milford, NJ (US); Lawrence Kiefer, Lafayette, NJ (US); Brian Gerard Donley, Solon, OH (US); Brian Adams, Iowa City, IA (US)

(73) Assignee: EXTREMITY MEDICAL, LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,856

(22) Filed: Apr. 21, 2015

(65) Prior Publication Data
US 2015/0223856 A1    Aug. 13, 2015

Related U.S. Application Data

(63) Continuation of application No. 12/802,187, filed on Jun. 1, 2010, now Pat. No. 9,017,329, which is a
(Continued)

(51) Int. Cl.
*A61B 17/70* (2006.01)
*A61B 17/86* (2006.01)
(Continued)

(52) U.S. Cl.
CPC ...... *A61B 17/8615* (2013.01); *A61B 17/1717* (2013.01); *A61B 17/1775* (2016.11);
(Continued)

(58) Field of Classification Search
CPC ............ A61B 17/8615; A61B 17/1717; A61B 17/7233; A61B 17/8605
See application file for complete search history.

(56) References Cited

U.S. PATENT DOCUMENTS 928,997 A * 7/1909 Muller .................... F16B 39/24
238/262
2,398,220 A * 4/1946 Gelpcke .............. F16B 13/0808
411/342
(Continued)

*Primary Examiner* — Ellen C Hammond
*Assistant Examiner* — Stuart S Bray
(74) *Attorney, Agent, or Firm* — Kelley Drye & Warren, LLP

(57) ABSTRACT

A method for applying compression to a joint includes providing an intramedullary fixation assembly having a proximal screw member positioned at a proximal end of the intramedullary fixation assembly and a lag screw member positioned at a distal end of the intramedullary fixation assembly. Medullary canals are drilled in a first and second bone and the medullary canals are reamed. The proximal screw member is inserted into the first bone and a drill is used create a dorsal hole in the first bone. The lag screw member is slideably coupled to the dorsal hole and to the proximal screw member and into the second medullary canal. A torque is applied to the lag screw member to apply compression to the joint.

18 Claims, 15 Drawing Sheets

Related U.S. Application Data continuation-in-part of application No. 12/456,808, filed on Jun. 23, 2009, now Pat. No. 8,303,589.

(60) Provisional application No. 61/132,932, filed on Jun. 24, 2008.

(51) Int. Cl.

| | | |
|---|---|---|
| A61B 17/72 | (2006.01) | |
| A61B 17/17 | (2006.01) | |
| A61F 2/42 | (2006.01) | |
| A61F 2/30 | (2006.01) | |

(52) U.S. Cl.
CPC .......... *A61B 17/72* (2013.01); *A61B 17/7233* (2013.01); *A61B 17/7291* (2013.01); *A61B 17/8605* (2013.01); *A61B 17/8625* (2013.01); *A61B 17/8685* (2013.01); *A61F 2/4241* (2013.01); *A61B 17/1782* (2016.11); *A61F 2002/3085* (2013.01); *A61F 2002/30622* (2013.01); *A61F 2002/4238* (2013.01); *A61F 2002/4248* (2013.01)

(56) References Cited

U.S. PATENT DOCUMENTS

| | | | | |
|---|---|---|---|---|
| 3,019,686 A | * | 2/1962 | Behrle | B65D 9/32 411/469 |
| 3,200,694 A | * | 8/1965 | Rapata | F16B 13/02 174/153 G |
| 3,411,398 A | * | 11/1968 | Blakeley | F16B 19/1054 411/41 |
| 3,474,537 A | * | 10/1969 | Christensen | A61C 8/0009 433/174 |
| 3,579,831 A | * | 5/1971 | Stevens | A61C 8/0009 433/174 |
| 4,463,753 A | * | 8/1984 | Gustilo | A61B 17/863 411/386 |
| 4,655,199 A | * | 4/1987 | Steffee | A61B 17/7055 606/246 |
| 4,795,294 A | * | 1/1989 | Takada | A47G 1/22 248/493 |
| 4,854,311 A | * | 8/1989 | Steffee | A61B 17/7058 411/389 |
| 4,930,963 A | * | 6/1990 | Rockenfeller | F16B 13/12 411/357 |
| 4,987,714 A | * | 1/1991 | Lemke | E04D 3/3603 411/369 |
| 5,336,225 A | * | 8/1994 | Zang | A61B 17/8605 411/398 |
| 5,496,322 A | * | 3/1996 | Mathews | A61B 17/70 606/279 |
| 5,501,557 A | * | 3/1996 | Wakai | F16B 13/124 411/55 |
| 5,857,816 A | * | 1/1999 | Assmundson | F16B 31/02 411/1 |
| 5,865,559 A | * | 2/1999 | Yang | E02B 3/062 403/320 |
| 5,904,683 A | * | 5/1999 | Pohndorf | A61B 17/7059 606/287 |
| 5,919,193 A | * | 7/1999 | Slavitt | A61B 17/1735 411/923 |
| 5,984,681 A | * | 11/1999 | Huang | A61C 8/001 433/173 |
| 6,174,119 B1 | * | 1/2001 | Orr | F16B 15/0053 411/461 |
| 6,187,005 B1 | * | 2/2001 | Brace | A61B 17/7035 606/264 |
| 6,247,883 B1 | * | 6/2001 | Monserratt | F16B 13/045 411/34 |
| 6,261,039 B1 | * | 7/2001 | Reed | B23P 6/04 411/178 |
| 6,379,362 B1 | * | 4/2002 | Birk | A61B 90/14 411/386 |
| 6,435,788 B2 | * | 8/2002 | Reed | Y10T 29/49734 29/402.11 |
| 6,517,541 B1 | * | 2/2003 | Sesic | A61B 17/72 606/62 |
| 6,632,057 B1 | * | 10/2003 | Fauchet | F16B 23/003 411/403 |
| 6,685,706 B2 | * | 2/2004 | Padget | A61B 17/683 411/517 |
| 6,695,844 B2 | * | 2/2004 | Bramlet | A61B 17/1659 606/282 |
| 6,743,018 B1 | * | 6/2004 | Morrow | A61C 8/005 411/55 |
| 6,908,271 B2 | * | 6/2005 | Breslin | F16B 13/126 411/271 |
| 6,981,974 B2 | * | 1/2006 | Berger | A61B 17/82 411/397 |
| 7,204,838 B2 | * | 4/2007 | Jackson | A61B 17/7032 606/270 |
| 7,524,326 B2 | * | 4/2009 | Dierks | A61B 17/7041 606/308 |
| 7,591,819 B2 | * | 9/2009 | Zander | A61B 17/72 411/508 |
| 7,901,435 B2 | * | 3/2011 | Slivka | A61B 17/7032 606/264 |
| 8,292,899 B2 | * | 10/2012 | Olsen | A61B 17/162 606/104 |
| 8,540,756 B2 | * | 9/2013 | Olsen | A61B 17/862 411/403 |
| 8,821,546 B2 | * | 9/2014 | Vaughan | A61B 17/1757 606/246 |
| 2002/0128712 A1 | * | 9/2002 | Michelson | A61F 2/446 623/17.11 |
| 2002/0197134 A1 | * | 12/2002 | Huber | B25B 13/48 411/551 |
| 2003/0147716 A1 | * | 8/2003 | Nagawa | F16B 35/041 411/288 |
| 2004/0193161 A1 | * | 9/2004 | Vaughan | A61B 17/1757 606/914 |
| 2005/0069397 A1 | * | 3/2005 | Shavit | A61B 17/744 411/457 |
| 2005/0107791 A1 | * | 5/2005 | Manderson | A61B 17/68 606/62 |
| 2006/0052787 A1 | * | 3/2006 | Re | A61F 2/0805 606/191 |
| 2006/0189991 A1 | * | 8/2006 | Bickley | A61B 17/864 606/916 |
| 2006/0200141 A1 | * | 9/2006 | Janna | A61B 17/72 606/62 |
| 2008/0221623 A1 | * | 9/2008 | Gooch | A61B 17/686 606/302 |
| 2008/0279654 A1 | * | 11/2008 | Deschamps | E04F 15/02 411/457 |
| 2009/0099571 A1 | * | 4/2009 | Cresina | A61B 17/17 606/96 |
| 2010/0010490 A1 | * | 1/2010 | Brigido | A61B 17/1725 606/64 |
| 2010/0256638 A1 | * | 10/2010 | Tyber | A61B 17/1717 606/62 |
| 2010/0256639 A1 | * | 10/2010 | Tyber | A61B 17/1717 606/62 |
| 2010/0324556 A1 | * | 12/2010 | Tyber | A61B 17/1717 606/62 |
| 2011/0009912 A1 | * | 1/2011 | Gonzalez-Hernandez | A61B 17/7208 606/328 |
| 2011/0022066 A1 | * | 1/2011 | Sevrain | A61B 17/86 606/151 |
| 2011/0054473 A1 | * | 3/2011 | Brigido | A61B 17/1725 606/62 |
| 2011/0087227 A1 | * | 4/2011 | Mazur | A61B 17/68 606/62 |
| 2011/0118739 A1 | * | 5/2011 | Tyber | A61B 17/1717 606/62 |
| 2011/0125153 A1 | * | 5/2011 | Tyber | A61B 17/1717 606/62 |

(56) References Cited

U.S. PATENT DOCUMENTS

| | | | |
|---|---|---|---|
| 2011/0166608 A1* | 7/2011 | Duggal | A61B 17/683 606/320 |
| 2011/0213367 A1* | 9/2011 | Tyber | A61B 17/1717 606/62 |
| 2011/0230884 A1* | 9/2011 | Mantzaris | A61B 17/1717 606/64 |
| 2011/0257652 A1* | 10/2011 | Roman | A61B 17/7225 606/62 |
| 2011/0276099 A1* | 11/2011 | Champagne | A61B 17/7225 606/328 |
| 2012/0065692 A1* | 3/2012 | Champagne | A61B 17/7291 606/311 |
| 2012/0197254 A1* | 8/2012 | Wolfe | A61B 17/1717 606/62 |
| 2012/0259419 A1* | 10/2012 | Brown | A61F 2/4225 623/21.19 |
| 2013/0066383 A1* | 3/2013 | Anderson | A61B 17/7233 606/329 |
| 2013/0123862 A1* | 5/2013 | Anderson | A61B 17/88 606/321 |
| 2013/0150903 A1* | 6/2013 | Vincent | A61B 17/86 606/301 |
| 2013/0238036 A1* | 9/2013 | Sinha | A61B 17/68 606/304 |
| 2014/0277554 A1* | 9/2014 | Roman | A61F 2/4225 623/21.19 |
| 2015/0150607 A1* | 6/2015 | Chen | A61B 17/1682 606/329 |
| 2015/0359580 A1* | 12/2015 | Dacosta | A61B 17/17 606/281 |
| 2016/0183988 A1* | 6/2016 | Simon | A61B 17/7291 606/64 |

* cited by examiner

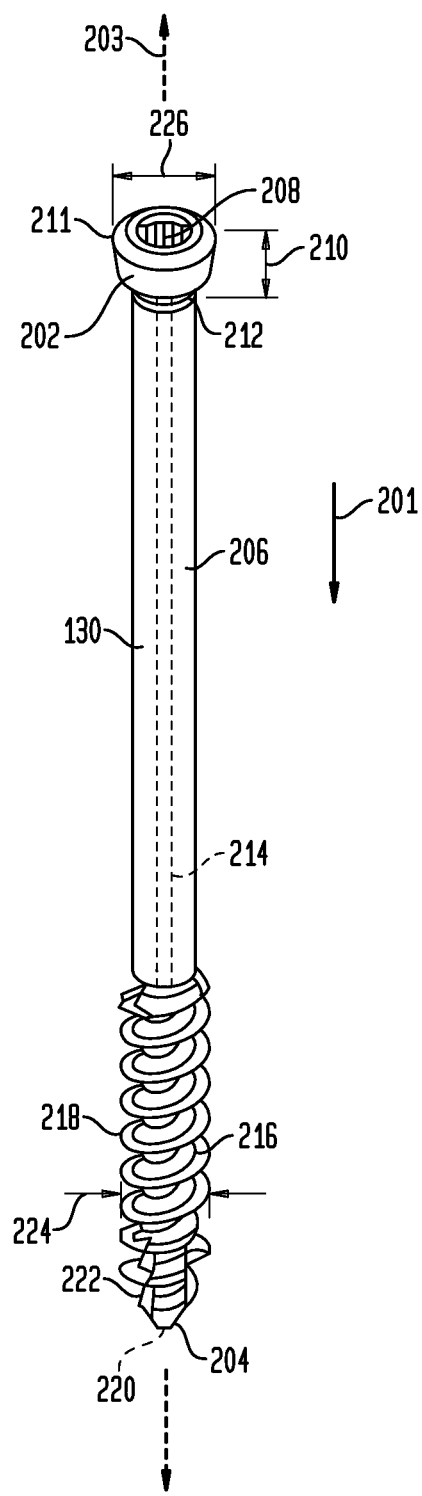

INTRAMEDULLARY FIXATION ASSEMBLY AND METHOD OF USE

CROSS-REFERENCE TO RELATED APPLICATIONS

This application is a continuation of U.S. patent application Ser. No. 12/802,187, filed Jun. 1, 2010, which is a continuation in part application claims the benefit of U.S. patent application Ser. No. 12/456,808, filed Jun. 23, 2009, now U.S. Pat. No. 8,303,589, issued Nov. 6, 2012, which claims the benefit of Provisional Application No. 61/132,932, filed Jun. 24, 2008, the entire contents of the entire chain of applications is herein incorporated by reference.

FIELD OF THE INVENTION

This invention relates to the field of orthopedic implant devices, and more particularly, to an intramedullary fixation assembly used for internal fixation of angled joints, bones and deformity correction, such as the metacarpal phalangeal joint in the hand.

BACKGROUND OF THE INVENTION

Orthopedic implant devices, such as intramedullary nails, plates, rods and screws are often used to repair or reconstruct bones and joints affected by trauma, degeneration, deformity and disease, such as Charcot arthropathy caused by diabetes in some patients. As an example, charcot arthropathy (or Charcot Foot) is a destructive process affecting many regions including joints of the foot and ankle in diabetics. This condition causes bony fragmentation, dislocation and fractures that eventually progresses to foot deformity, bony prominences, ulceration and instability of the foot. Charcot arthropathy can affect any joint in the body but is often seen in the feet affecting the metatarsal, tarsometatarsal and tarsal joints and frequently causes the foot to lose its arch or curvature, thus resulting in "flat footedness" in the mid-foot region.

Early treatment for Charcot Foot includes the use of therapeutic footwear, immobilization of the foot and/or non-weight bearing treatment. Surgical treatments include orthopedic fixation devices that fixate the bones in order to fuse them into a stable mass. These orthopedic implant devices realign bone segments and hold them together in compression until healing occurs, resulting in a stable mass.

Various implants have been utilized for surgical treatment, including bone screws. While these devices allow fixation and promote fusion, they do not deliver restoration of the arch in a Charcot Foot. Instead, the physician must estimate the arch and manually align the bones and deliver the screws to hold the bones in place, while reducing bone purchase. Intramedullary nails and/or a plate with a lag screw too have deficiencies. These intramedullary nails also do not reconstruct an arch that is lost due to Charcot foot disease.

Moreover, infections and wound complications are a major concern in aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

There is therefore a need for an intramedullary fixation assembly and method of use that overcomes some or all of the previously delineated drawbacks of prior fixation assemblies.

SUMMARY OF THE INVENTION

An object of the invention is to overcome the drawbacks of previous inventions.

Another object of the invention is to provide a novel and useful intramedullary fixation assembly that may be utilized to treat any bones in human body.

Another object of the invention is to provide a novel and useful intramedullary fixation assembly that may be utilized to treat bones in a mid-foot region.

Another object of the invention is to restore the arch by utilizing an intramedullary assembly.

Another object of the invention is to provide a system for treating deteriorating bones in a mid-foot region.

Another object of the invention is to provide a method for restoring the arch of the foot by delivering a fixator that can be coupled in a patient's foot.

Another object of the invention is to provide a connecting mechanism for generating compression in a patient's hand and foot bones.

Another object of the invention is to utilize a torque in the connecting mechanism to transmit compression to the bones in a patient's hand and foot bones.

In a first non-limiting aspect of the invention, a fixation assembly comprising two members is provided. A first member, positioned at a proximal end of the fixation assembly, has an elongated portion and a tapered bulbous end. A second member, positioned at a distal end of the fixation assembly, has an internal tapered aperture, wherein the elongated portion resides within the internal tapered aperture. The first member forms a fixed angle with the second member, thereby selectively coupling the first member to the second member.

In a second non-limiting aspect of the invention, a method for reconstructing an arch in a mid-foot region comprises eight steps. Step one includes making an incision in the mid-foot region of a patient's foot. Step two includes gunstocking the foot to expose the articular surface. Step three includes reaming the intramedullary canal and inserting a distal member. Step four includes coupling the instrument to the distal member. Step five includes assessing the position of the proximal member with a guide wire. Step six includes pre-drilling a hole through the joints selected for fusion. The seventh step includes inserting the proximal member over the guide wire until rigid connection with the tapered aperture is made that compresses the joint and wherein the proximal member is at an angle to the distal member. The eighth step includes removing the instrument and closing the incision, thereby causing the arch to be formed in the mid-foot region.

In a third non-limiting aspect of the invention, an instrument is combined with a fixation assembly for reconstructing an arch in a mid-foot region. The instrument has a handle, a "U-shaped" recess having two sides and a tapered bore. The intramedullary fixation assembly has a first member and a second member. The first member is positioned at a proximal end of the intramedullary fixation assembly. The first member has an elongated portion and a bulbous portion. The second member is positioned at a distal end of the intramedullary fixation assembly. The second member has an internal tapered aperture, a plurality of grooves and a threaded portion. The elongated portion resides within the internal tapered aperture, and a "U-shaped" recess having two sides that couple the first member to the second member, and further coupling the instrument to the intramedullary fixation assembly for reconstructing the arch in the mid-foot region.

In a fourth non-limiting aspect of the invention, a method for joint compression in a human hand comprises eight steps. Step one includes providing an intramedullary fixation assembly. Step two includes drilling a first medullary canal in a first bone and drilling a second medullary canal in a second bone. Step three includes reaming the first medullary canal of the first bone and the second medullary canal of the second bone. Step four includes inserting the proximal screw member into the first bone. Step five includes inserting a drill in the proximal screw member and creating a dorsal hole in the first bone at a predetermined angle. Step six includes slideably coupling the lag screw member into the dorsal hole and into the proximal screw member to lock the lag screw member to the proximal screw member. Step seven includes threadably coupling the lag screw member into the second medullary canal. Step eight includes applying torque to the lag screw member to cause compression of the joint.

In a fifth non-limiting aspect of the invention, a method for applying compression to a joint includes eight steps. Step one includes providing an intramedullary fixation assembly, where the intramedullary fixation assembly further includes a proximal screw member positioned at a proximal end of the intramedullary fixation assembly and a lag screw member positioned at a distal end of the intramedullary fixation assembly, where the proximal screw member is slideably coupled to the lag screw member and makes a fixed angle with the lag screw member. Step two includes drilling a first medullary canal in a first bone and drilling a second medullary canal in a second bone. Step three includes reaming the first medullary canal of the first bone and the second medullary canal of the second bone. Step four includes inserting the proximal screw member into the first bone. Step five includes inserting a drill in the proximal screw member and creating a dorsal hole in the first bone at a predetermined angle. Step six includes slideably coupling the lag screw member into the dorsal hole and into the proximal screw member to lock the lag screw member to the proximal screw member. Step seven includes threadably coupling the lag screw member into the second medullary canal. Step eight includes applying torque to the lag screw member to cause compression of the joint.

In a sixth non-limiting aspect of the invention, an intramedullary fixation assembly for bone fusion includes a proximal screw member positioned at a proximal end of the intramedullary fixation assembly and a lag screw member positioned at a distal end of the intramedullary fixation assembly. The proximal screw member includes a tapered aperture aligned at a predetermined angle, where the proximal screw member is slideably coupled to the lag screw member at the predetermined angle.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which:

FIG. 2 is a perspective view of a proximal screw member used in the fixation system shown in FIG. 1 according to the preferred embodiment of the invention.

DETAILED DESCRIPTION OF THE INVENTION

The invention may be understood more readily by reference to the following detailed description of preferred embodiment of the invention. However, techniques, systems and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
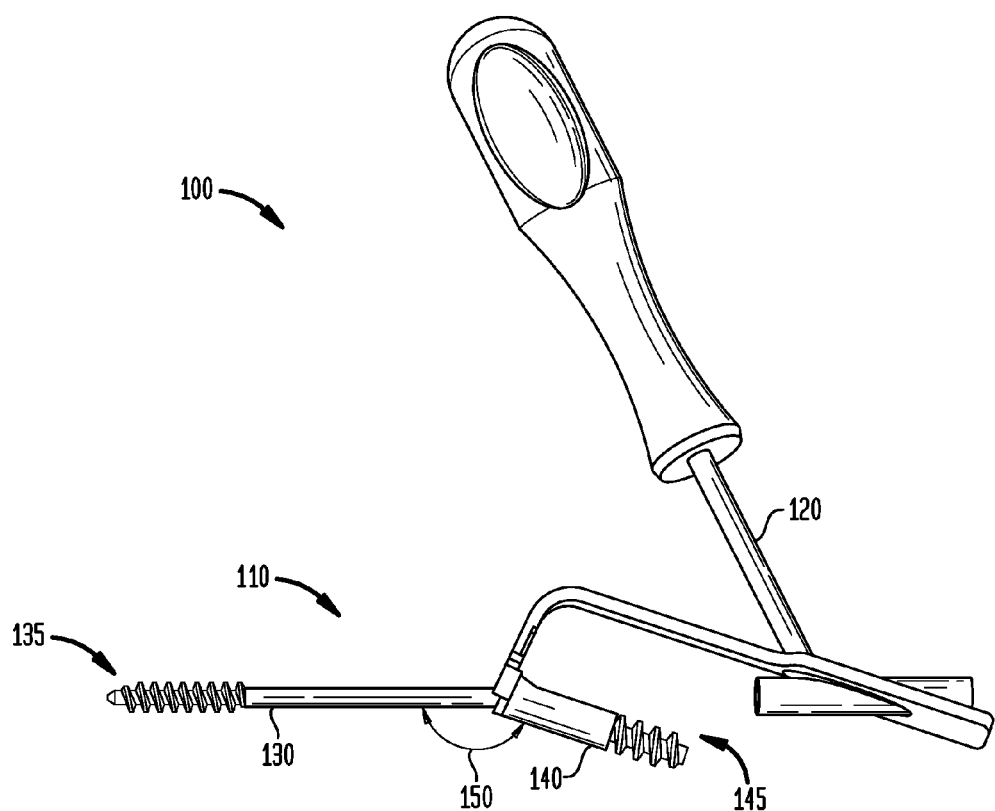
FIG. 1 is a perspective view of a fixation system according to a preferred embodiment of the invention.

Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones, in one non-limiting example, in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST, PEEK, NiTi, Cobalt chrome or other similar types of materials. It should also be appreciated that intramedullary fixation assembly 110 may be utilized for the internal fixation of other bones in the human body.

As shown in FIG. 2, proximal screw member 130 is generally cylindrical in shape and extends from first bulbous portion 202 to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 when tapered bulbous portion 202 is combined with tapered aperture 316, shown and described below. Moreover, bulbous portion 202 is generally circular and has a generally hexagonal torque-transmitting aperture 208 that traverses length 210 of bulbous portion 202. However, a star-shaped aperture, a square-shaped aperture, or any other shaped aperture may be utilized without departing from the scope of the invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 comprises an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in a foot (not shown).

Figure 3A:
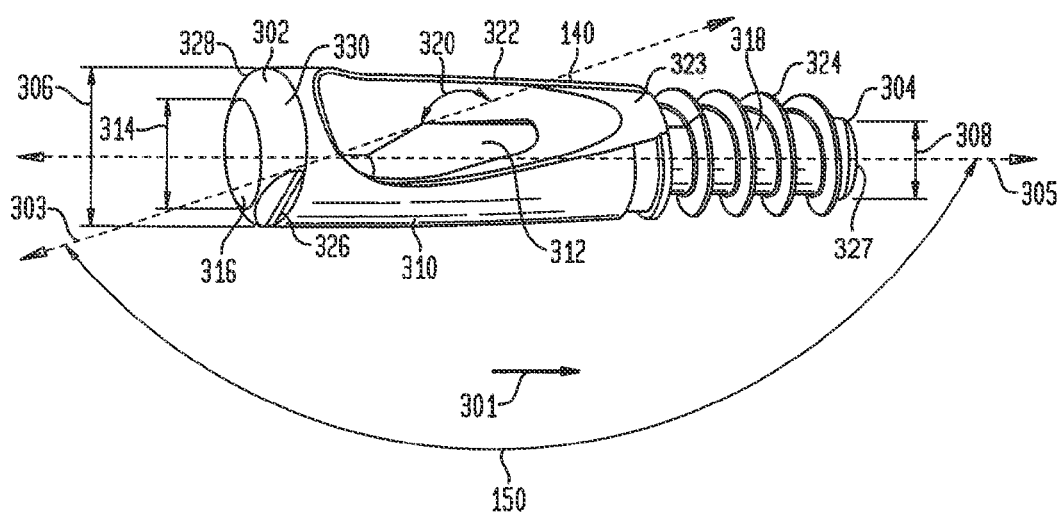
FIG. 3A is a perspective view of a distal member used in the fixation system shown in FIG. 1 according to the preferred embodiment of the invention.
Figure 3B:
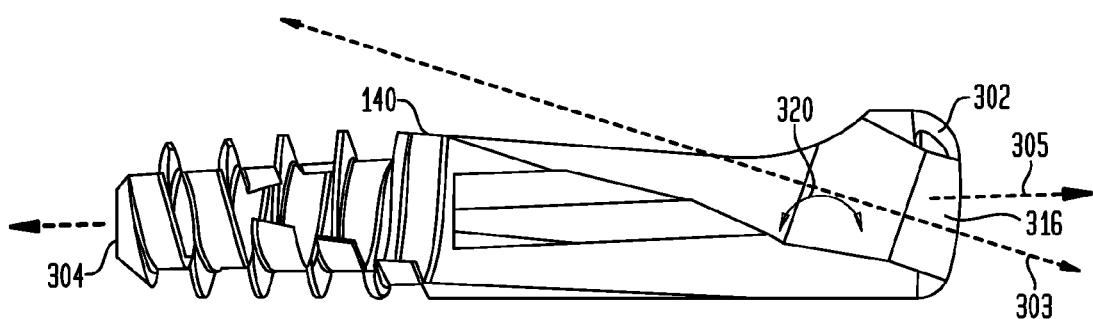
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 comprises slope 320 from first end 302 to end 323 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further comprises a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 327 which is longitudinally coextensive with portion 318 in direction 301. Circular aperture 327 aligns with aperture 312 to form a continuous opening from end 302 to end 304.

Figure 4:
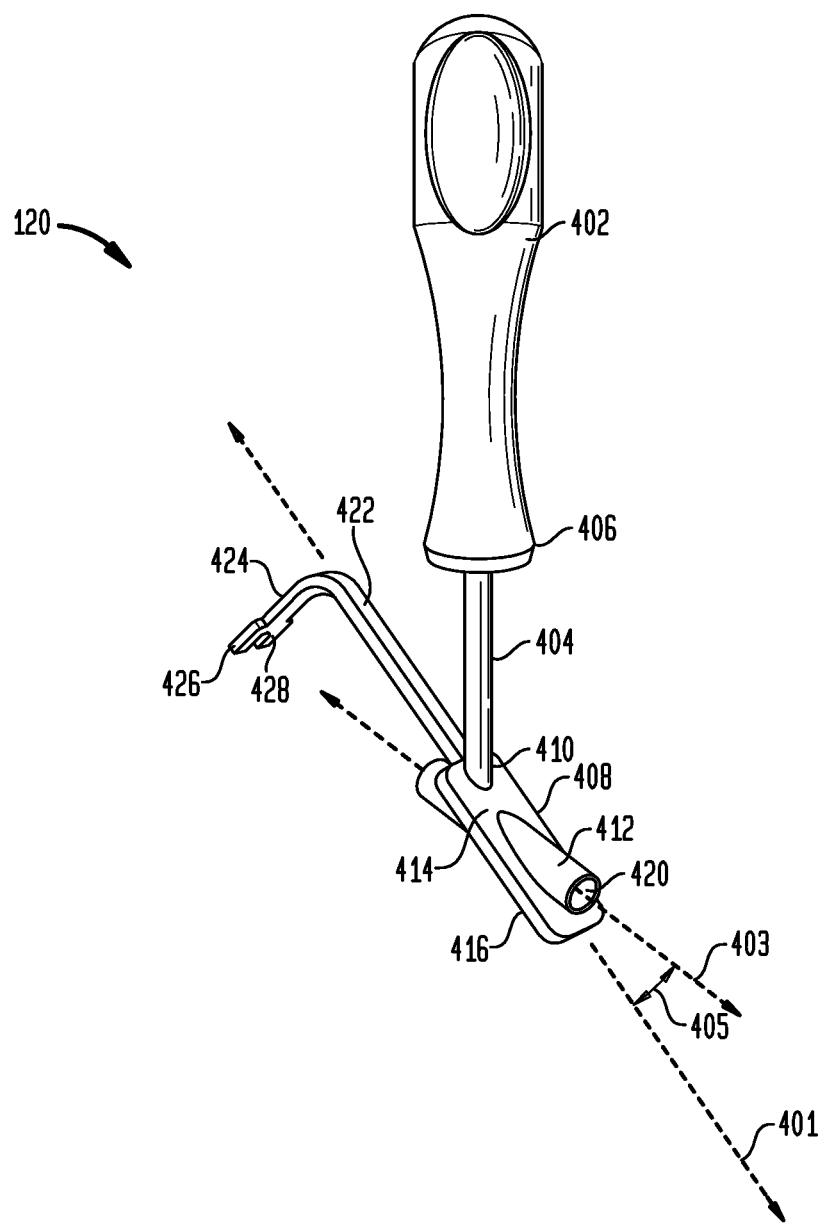
FIG. 4 is a perspective view of the instrument member used in the fixation system shown in FIG. 1 according to the preferred embodiment of the invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device). Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120.

Figure 5:
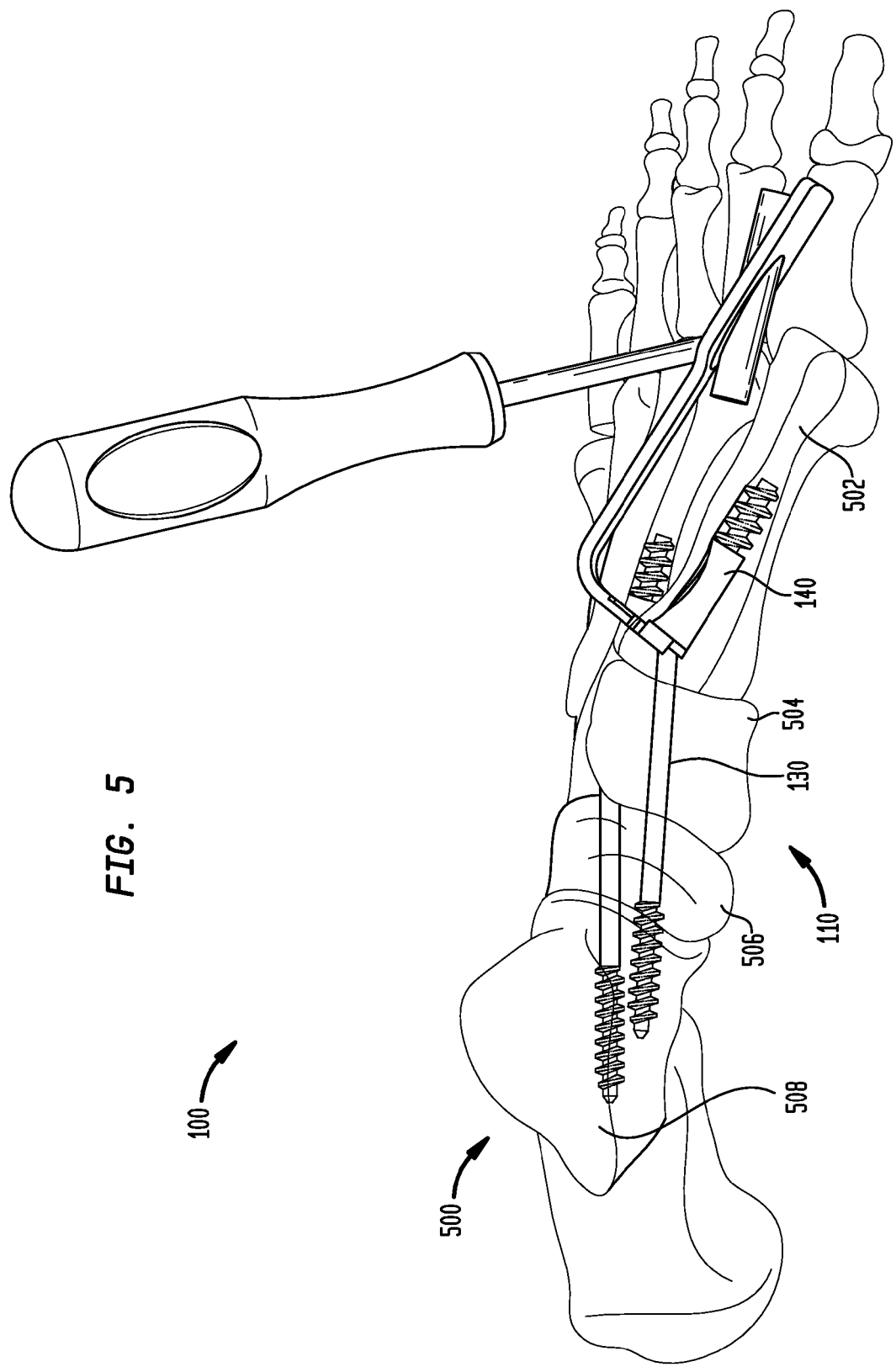
FIG. 5 is a perspective view of the assembled intramedullary fixation assembly inserted into the bones of a patient's foot according to the preferred embodiment of the invention.
Figure 6:
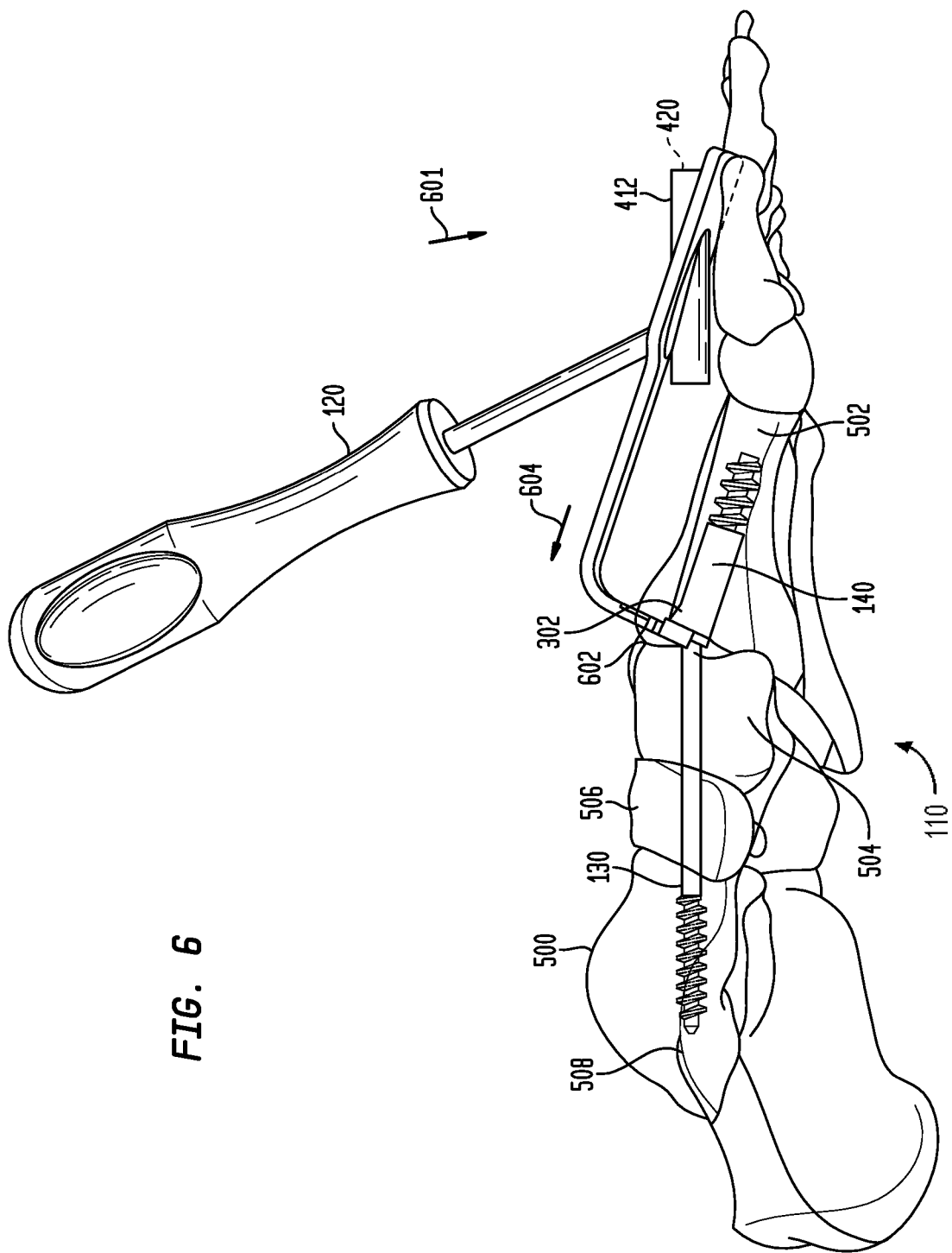
FIG. 6 is a side view of the assembled intramedullary fixation assembly shown in FIG. 5 according to the preferred embodiment of the invention.
Figure 7:
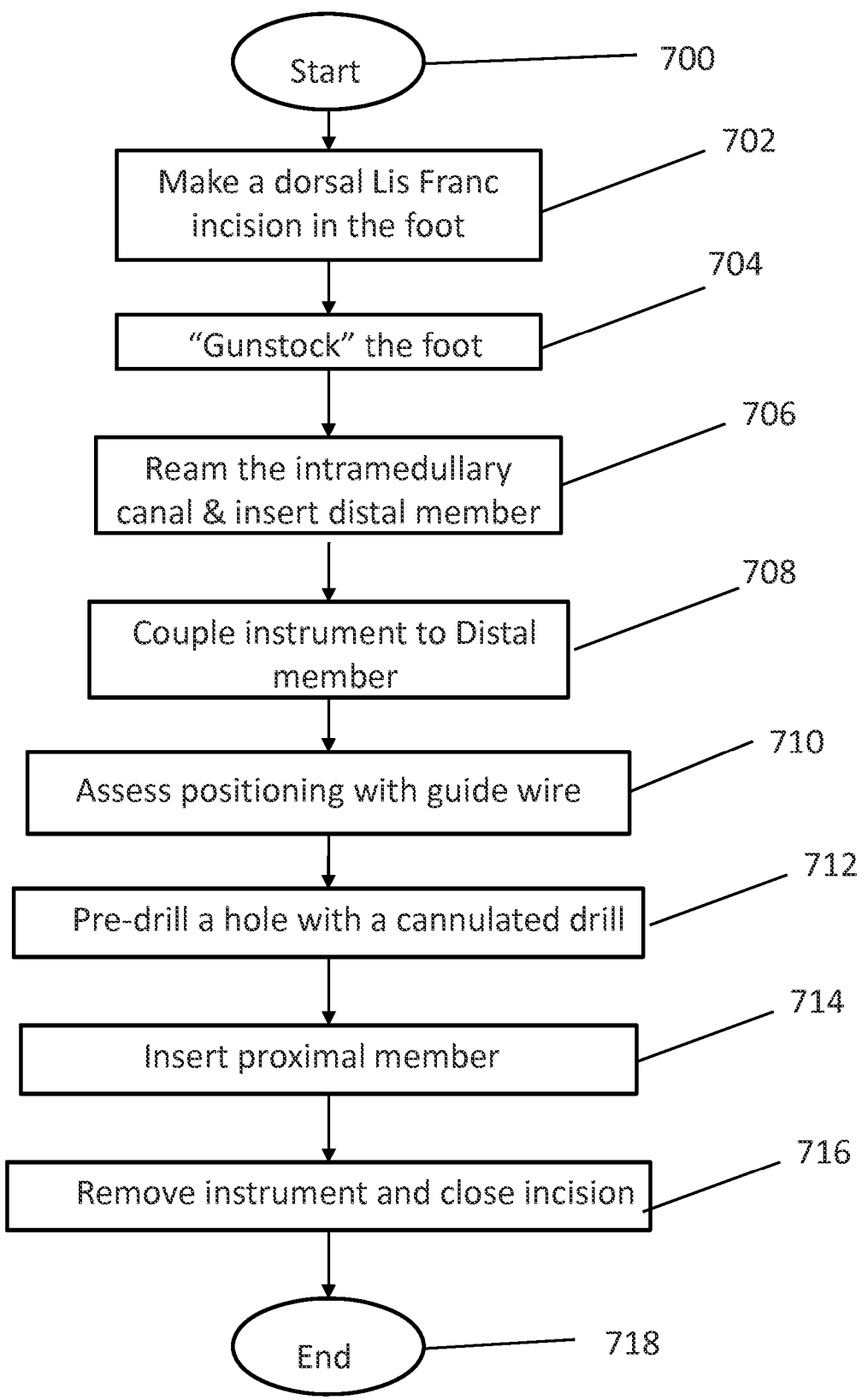
FIG. 7 is a flow chart illustrating the method of coupling the intramedullary fixation assembly shown in FIGS. 1-6 to tarsal and metatarsal bones in a human foot according to the preferred embodiment of the invention.

In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray. In one non-limiting example, the angulation may be any angle greater than 90 degrees and less than 180 degrees. For example, the angle for the first ray may be 150-170 degrees and the angles for the other rays may be 160-175 degrees. As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary canal (not shown) of the metatarsal 502. In other non-limiting embodiments, the distal member 140 may be inserted by impaction, by press fit, by reaming a hole in the intramedullary canal (not shown) or substantially any other similar strategy or technique.

Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboid, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

Figure 8:
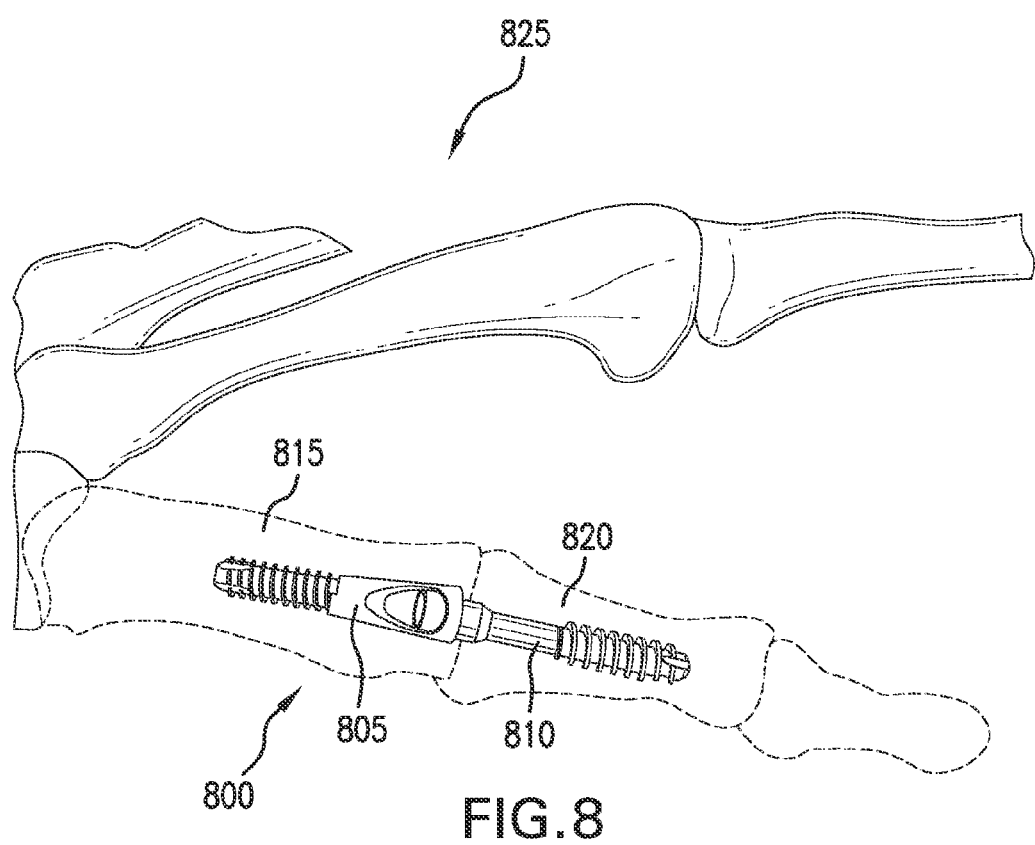
FIG. 8 is a perspective view of an assembled intramedullary fixation assembly inserted into the metacarpal and proximal phalangeal bones of a patient's hand according to an alternate embodiment of the invention.

In an alternate embodiment, as shown in FIG. 8, an intramedullary fixation assembly 800 may comprise interconnected members for applying compression to, in one example, the metacarpal bone 815 and the first proximal phalange bone 820 in the human hand 825 or any other appropriate use for the internal fixation of the other bones in the human body. Particularly, the interconnected members include a metacarpal screw member 805 inserted into the medullary canal of the first metacarpal bone 815 and being coupled to a lag screw member 810 inserted into the first proximal phalange bone 820 for the internal fixation of the bones in the human hand 825. It should be appreciated that in one non-limiting embodiment, intramedullary fixation assembly 800 may be made from a Titanium material, although, in other non-limiting embodiments, intramedullary fixation assembly 800 may be made from SST, PEEK, NiTi, Cobalt chrome or other similar types of materials.

Figure 9A:
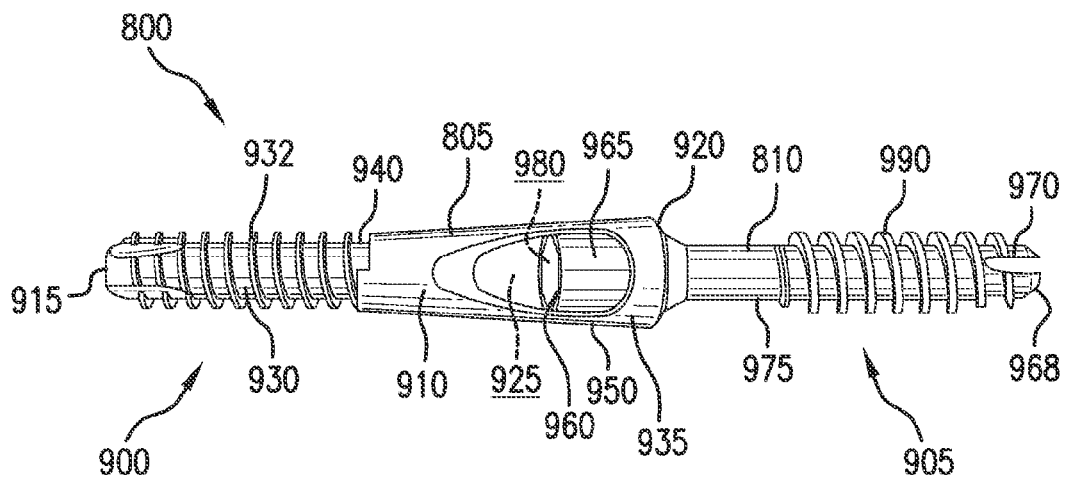
FIG. 9A is a perspective view of the intramedullary fixation assembly shown in FIG. 8 according to an embodiment of the invention.
Figure 9B:
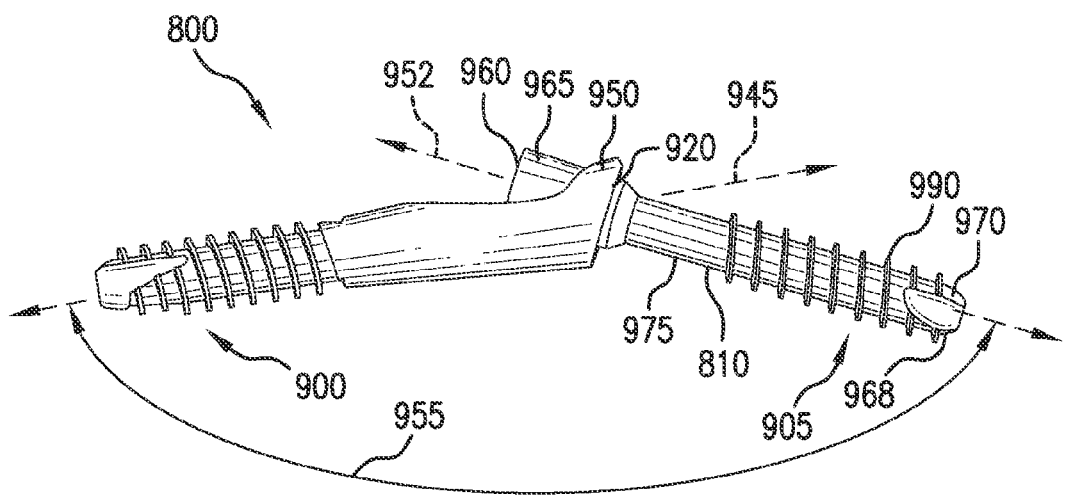
FIG. 9B is another perspective view of the intramedullary fixation assembly shown in FIGS. 8 and 9A according to an embodiment of the invention.

As shown in FIGS. 9A-9B, the intramedullary fixation assembly 800 includes metacarpal screw member 805 coupled to the lag screw member 810 through a frictional interference fit, with the metacarpal screw member 805 provided on the proximal end 900 of the fixation assembly 800 and the lag screw member 810 provided on the distal end 905. As shown in FIG. 9A, metacarpal screw member 805 is substantially similar to the distal member 140 shown in FIG. 1 and includes a generally tubular shaped body 910 having a threaded portion 930 terminating in a generally tubular portion 935. Threaded portion 930 has a generally uniform width from end 915 to end 940 and includes a plurality of circumferentially disposed threads 932 on the exterior surface of portion 930. Also, tubular portion 935 has a generally smooth exterior surface 950 and tapers from end 940 to end 920 (i.e., end 920 has a circumference that is slightly larger than circumference at end 940), although in another non-limiting embodiment, portion 935 may have a constant width from end 940 to end 920. Further, end 920 is inclined at 25-degrees (FIG. 9B) in order to align the metacarpal screw member 805 along the metacarpal phalangeal (MCP) joint, however in another non-limiting example, end 920 may be straight. Further, and as shown in FIG. 9B, tubular portion 935 has an internal aperture 925, which is aligned along axis 952 (FIG. 9B), which is offset from horizontally axis 945 of metacarpal screw member 805. Internal aperture 925 is generally circular, however, any other shaped aperture may be utilized without departing from the scope of the invention. Axis 952 forms a predetermined angle 955 with horizontal axis 945, causing aperture 925 to be tapered at the predetermined angle 955 and which determines the angle for fixation of the lag screw member 810 within the metacarpal screw member 805 (i.e., the predetermined angle 955 determines the angle for fusing the MCP joint). In one non-limiting embodiment, angle 955 may be fixed at 155 degrees although, in other non-limiting embodiments, the angle may be fixed at 160 degrees or substantially any other angle for the other rays of the human hand.

Also as shown in FIGS. 9A-9B, lag screw member 810 is generally cylindrical in shape and extends from bulbous portion 965 to a tapered end 968 on generally cylindrical portion 975. Portion 965 has a diameter that is slightly larger than the diameter of cylindrical portion 975. End 960 of bulbous portion 965 has a generally hexagonal torque transmitting aperture 980 (FIG. 9A), which is provided to transmit a torque from bulbous portion 965 to tapered end 968, although, in other non-limiting embodiments, aperture 980 may include a star-shaped aperture, a square-shaped aperture or any other shaped aperture may be utilized without departing from the scope of the invention. Also, portion 975 includes a self-tapping and self drilling leading edge 970, although in other non-limiting embodiments, a self-drilling edge may be provided in lieu of the self-tapping edge to provide the surgeon with the ability to remove bone material during insertion of lag screw member 810 into bone. Bulbous portion 965 has a taper, such as a Morse taper, which provides for a locked interference fit with internal aperture 925. Torque transmitting aperture 980 is utilized for transmitting a torque from bulbous portion 965 to self-tapping end 970 by rotating bulbous portion 965, causing the morse taper to lock within aperture 925 and convert the torque to a compressive force between the metacarpal screw member 805 and lag screw member 810 causing the underlying metacarpal joint to be compressed in the process.

Furthermore, lag screw member 810 may comprise an internal aperture (not shown) that is longitudinally coextensive with lag screw member 810 and form a continuous opening from end 960 to end 968 (i.e., lag screw member 810 is cannulated). The continuous opening or cannula is provided to interact with a guide wire (not shown) by receiving the guide wire within the continuous opening thereby positioning and locating the lag screw member 810. In other non-limiting embodiments, the lag screw member 810 may be solid). Also, lag screw member 810 has a plurality of circular threads, such as threads 990, which are circumferentially disposed on the external surface of portion 975 in order to facilitate traversal of lag screw member 810 into bone and apply compression by preventing linear motion being converted to rotary. It should be appreciated that the length of the lag screw member 810 may be selected of varying lengths to allow a surgeon to fuse different metacarpal joints in a hand or any other joints in the body (not shown).

Figure 10A:
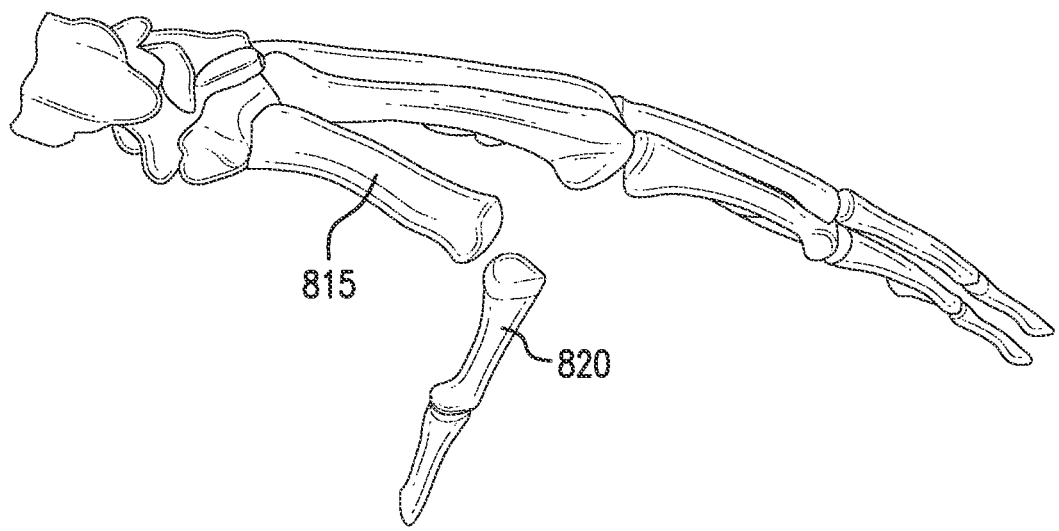
FIG. 10A is a perspective view of the surgical process being utilized on the metacarpal and phalangeal bones of a human hand using the intramedullary fixation assembly according to an embodiment of the invention.
Figure 10B:
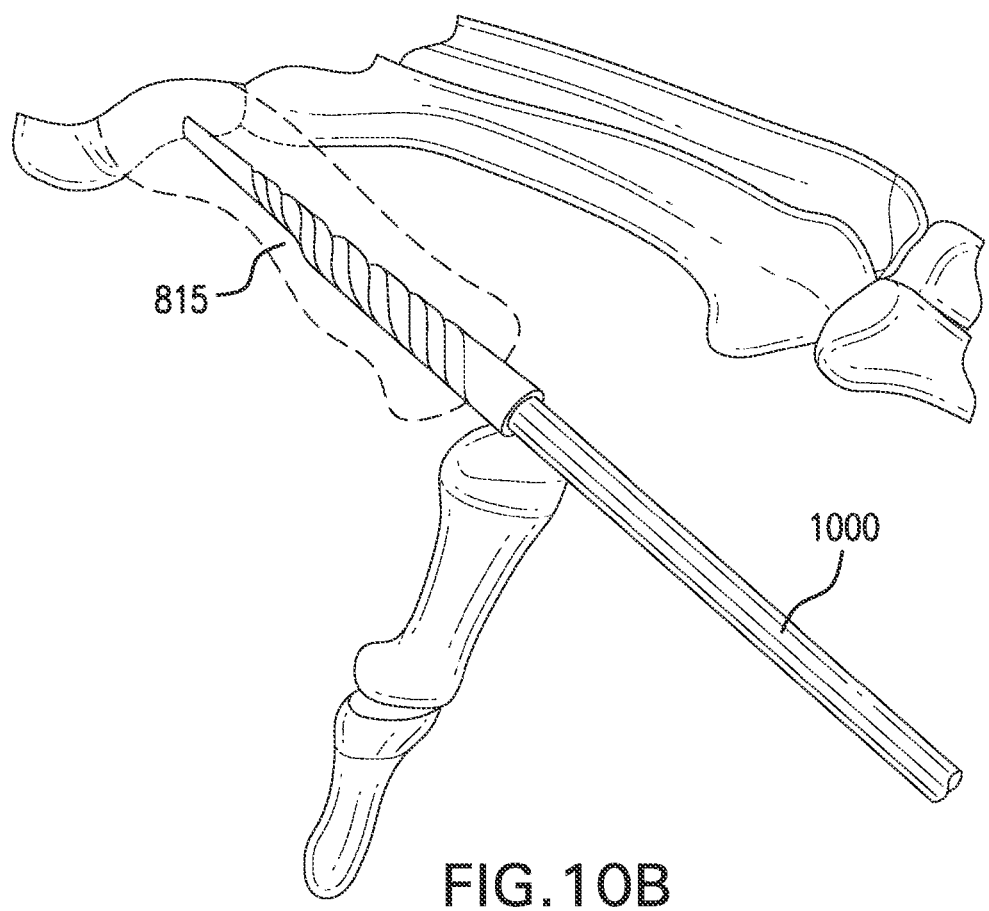
FIG. 10B is a perspective view of the surgical process of reaming the metacarpal bone of a human hand according to an embodiment of the invention.
Figure 10C:
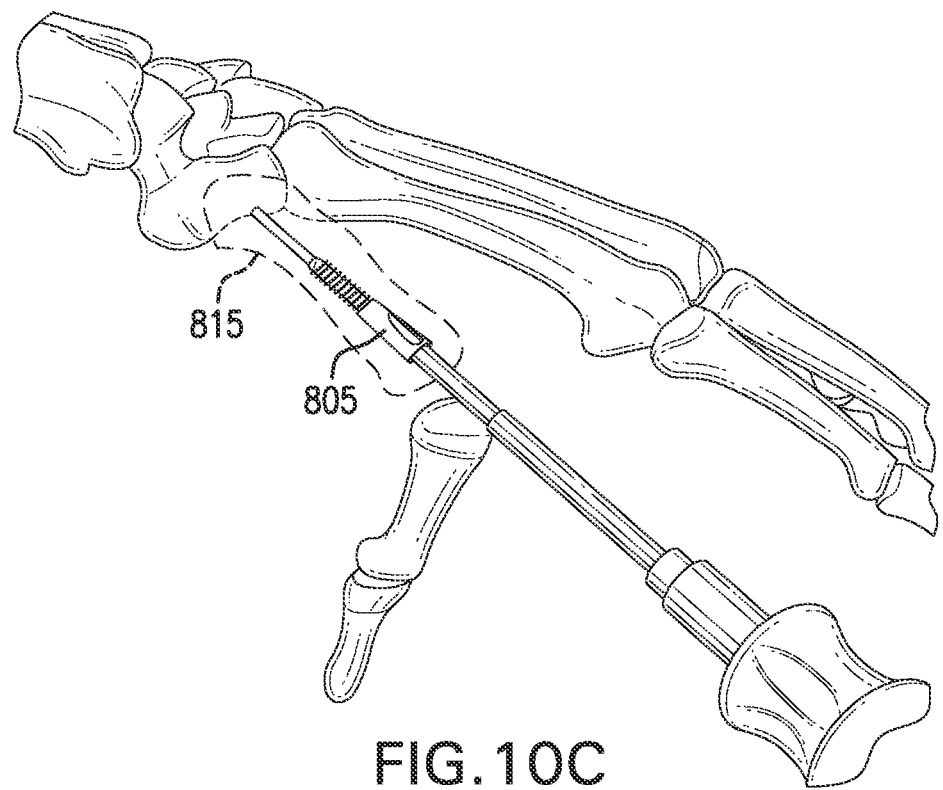
FIG. 10C is a perspective view of the surgical process of inserting the metacarpal screw member in the metacarpal bone of a human hand according to the embodiment of the invention.
Figure 10D:
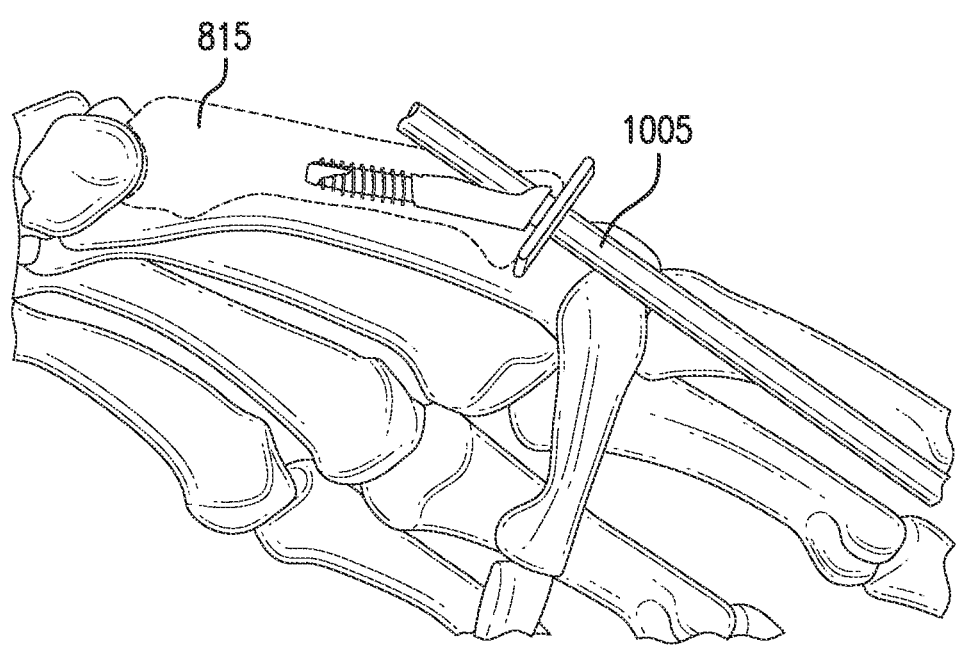
FIG. 10D is a perspective view of the surgical process of creating a dorsal window in the metacarpal bone of a human hand according to an embodiment of the invention.
Figure 10E:
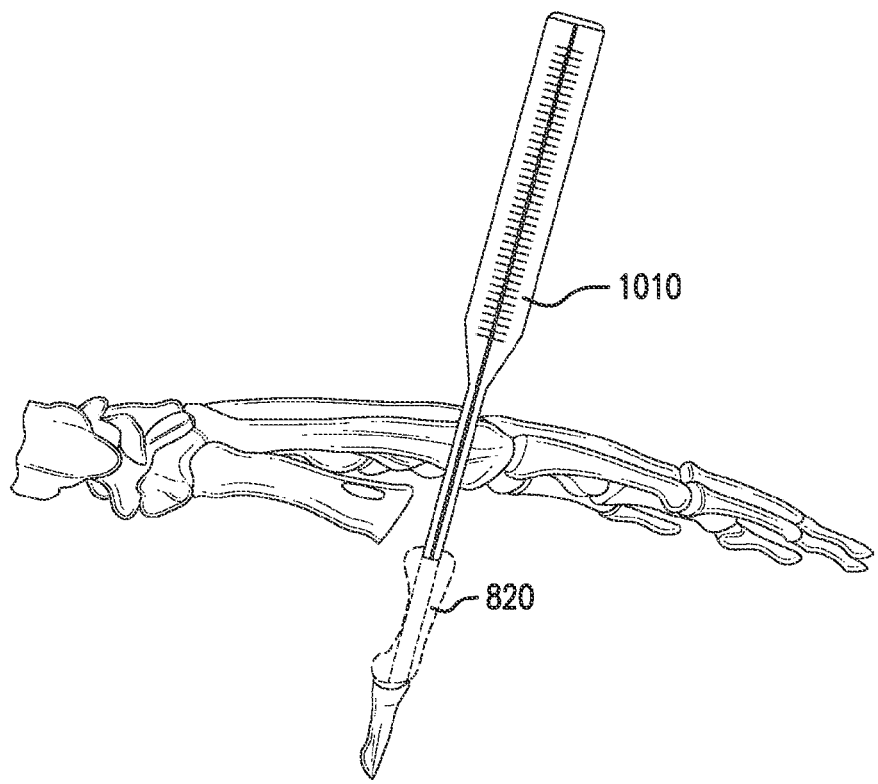
FIG. 10E is a perspective view of the surgical process of measuring the lag screw member depth in the phalangeal bone of a human hand according to an embodiment of the invention.
Figure 10F:
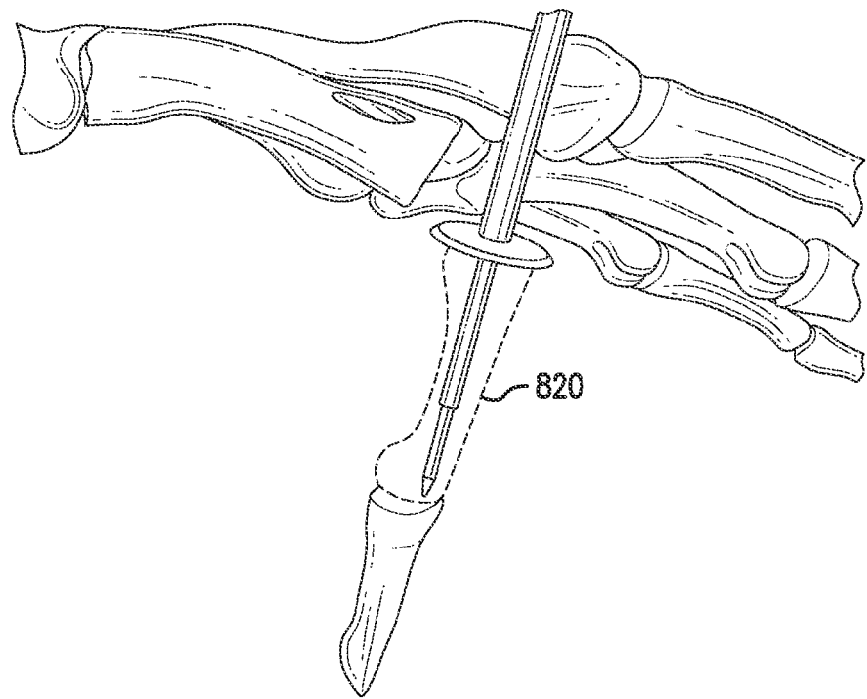
FIG. 10F is a perspective view of the surgical process of reaming the phalangeal bone of a human hand according to an embodiment of the invention.

As shown in FIGS. 8, 10A-H and 11, the intramedullary fixation assembly 800 may be utilized to selectively apply compression to the bones in a human hand 825, such as, for example, the first metacarpal bone 815 and the first proximal phalange bone 820. As shown, the method starts in step 1100 and proceeds to step 1102, whereby a Medial incision (not shown) is made in hand 825 in order to gain access to the metacarpophalangeal (MCP) joint. In step 1104, the joint capsule is separated by distracting the MCP joint (FIG. 10A) to expose the articular surfaces of the first metacarpal 815 and the first proximal phalange 820 and the articulating cartilage may be removed prior to insertion of the guidewire. Next, in step 1106, a guide wire is inserted into the first metacarpal bone 815 in order to predrill a hole through the intramedullary canal and, in step 1108, the intramedullary canal of the first metacarpal bone 815 is reamed at a predetermined depth with a reamer 1000 (FIG. 10B). Next, in step 1110, the metacarpal screw member 805 is inserted into the intramedullary canal (not shown) of the first metacarpal bone 815 and threadably connected at a predetermined depth in the intramedullary canal of the metacarpal bone 815 with aperture 925 (FIG. 9A) positioned in a dorsal position (FIG. 10C) or desired fusion angle in the intramedullary canal. It should be appreciated that in other non-limiting embodiments, the metacarpal screw member 805 may be inserted by impaction, by press fit, or by substantially any other similar strategy or technique. It should also be appreciated that the metacarpal screw member 805 may be inserted into the metacarpal bone 815 until the screw member 805 is flush with or slightly recessed below the cut surface of the metacarpal bone 815.

Figure 10G:
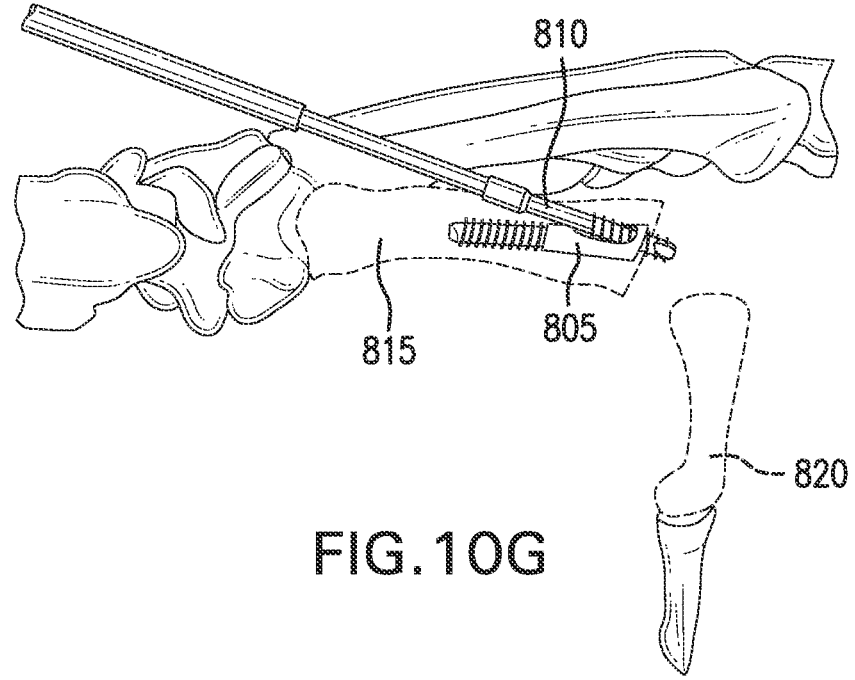
FIG. 10G is perspective view of the surgical process of inserting the lag screw member into the metacarpal screw member according to an embodiment of the invention.
Figure 10H:
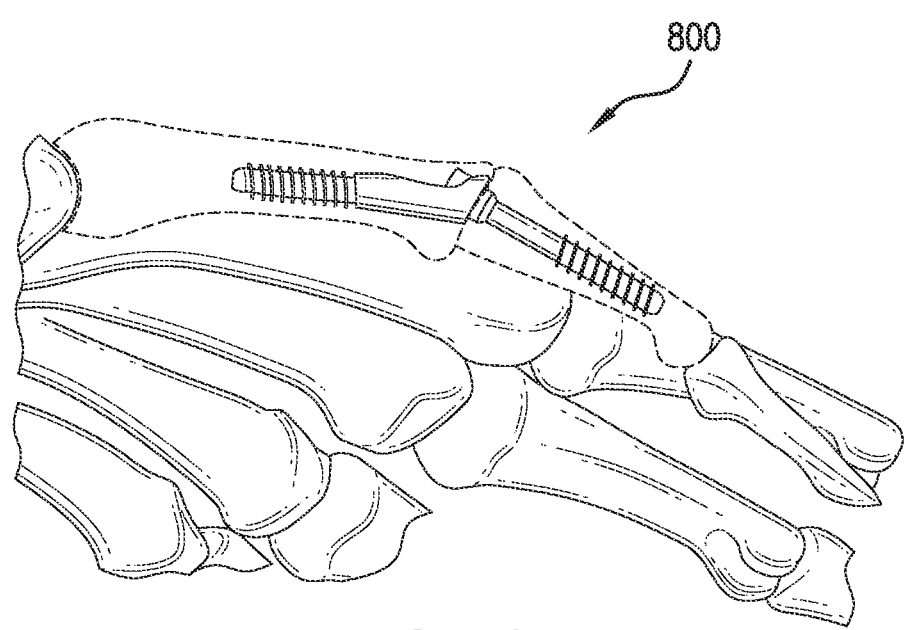
FIG. 10H is a perspective view of the inserted intramedullary fixation assembly shown in FIG. 8 according to an embodiment of the invention.
Figure 11:
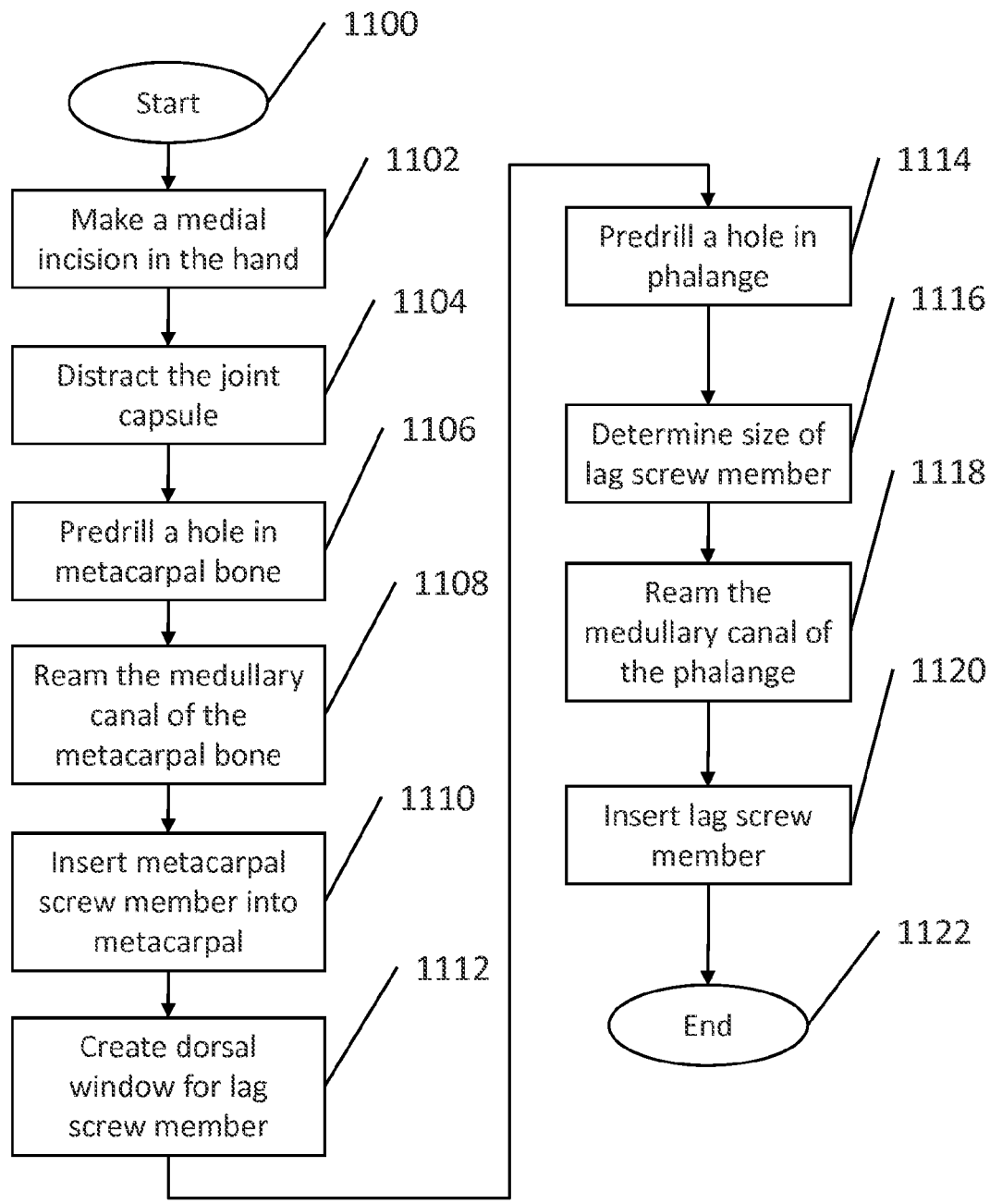
FIG. 11 is a flow chart illustrating the method of coupling the intramedullary fixation assembly shown in FIGS. 8-10H to the metacarpal and phalangeal bones in a human hand according to an embodiment of the invention.

Next, in step 1112, the metacarpal joint is prepared for fusion by creating a dorsal window in the metacarpal bone 815 (FIG. 10D) for receiving the lag screw member 810 (not shown) by using instrument 1005. The instrument 1005 is utilized to penetrate the dorsal surface of the metacarpal bone 815 at the predetermined angle 955, which determines the angle for joint fusion. Next, in step 1114, a guide wire is used to pre-drill a hole through the first proximal phalange bone 820 and the proximal cortex is penetrated. In step 1116, the size of the lag screw member 810 is chosen by inserting a lag screw depth gauge 1010 (FIG. 10E) over the lag screw and into the intramedullary canal of the first proximal phalange bone 820. Also, a lag screw rasp (not shown) may be utilized to create a flattened surface of bleeding bone by advancing the rasp over the guide wire (FIG. 10F) and removing bone material from the articulating surface. The rasp is removed and the guide wire is left in the first proximal phalange bone 820. Next, in step 1118, the metacarpal bone 815 is prepared for joint fusion by reaming the dorsal window of the metacarpal bone 815 (FIG. 10G). In step 1120, lag screw member 810 is inserted into the metacarpal screw member 805 through the dorsal window and into the first proximal phalange bone 820, aligning the bone 820 and compressing the metacarpal joint. Next, in step 1122, the metacarpal joint is verified (FIG. 10H) for proper alignment of the intramedullary fixation assembly 800. The method ends in step 1122.

It should be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A method for fusing the metacarpophalangeal joint, comprising the steps of:
   providing a first screw member comprising a first shaft extending along a first longitudinal axis and a bore extending through the first shaft along a bore axis;
   providing a second screw member comprising a head portion and a second shaft extending along a second longitudinal axis;
   forming a first bore hole in a metacarpal bone;
   inserting the first screw member into the first bore hole;
   forming a second bore hole in a phalange bone;
   inserting the second screw member into the second bore hole;
   coupling the second screw member to the first screw member; and
   applying torque to the head portion of the second screw member to lock the second screw member to the first screw member, thereby compressing the phalange bone;
   wherein the first longitudinal axis and the bore axis define an angle,
   wherein the second screw member is adapted for coupling to the first screw member at the angle, and
   wherein the first screw member is adapted for residing substantially within the metacarpal bone and the second screw member is adapted for residing substantially within the phalange bone.

2. The method of claim 1, wherein the first shaft of the first screw member extends from a first terminal end to a second terminal end, wherein the first screw member comprises a first aperture at the first terminal end, and wherein the bore extends through the first aperture and a second aperture in a side of the first screw member.

3. The method of claim 2, wherein the second screw member couples to the first screw member by being inserted through the second aperture and through the bore and out the first aperture until the head portion abuts the first aperture.

4. The method of claim 1, wherein the bore comprises a first taper and wherein the head portion comprises a second taper.

5. The method of claim 4, further comprising forming an interference fit with the first taper and the second taper.

6. The method of claim 1, wherein at least one of the first shaft of the first screw member and the second shaft of the second screw member comprise a threaded portion.

7. The method of claim 6, wherein the threaded portion comprises a plurality of bone threads on its outer surface.

8. The method of claim 6, wherein the threaded portion comprises a self-tapping or a self-drilling edge for removing bone material.

9. The method of claim 1, wherein the first screw member comprises a tapered portion at a first terminal end.

10. The method of claim 9, wherein the bore is in the tapered portion.

11. The method of claim 1, wherein applying torque to the head portion of the second screw member provides an interference fit between the second screw member and the first screw member, thereby fusing the metacarpophalangeal joint.

12. The method of claim 1, further comprising an aperture extending at least partially through at least one of the first screw member along the first longitudinal axis and the second screw member along the second longitudinal axis.

13. The method of claim 12, wherein the aperture comprises a hexagonal shape, a star shape, or a square shape.

14. The method of claim 12, wherein the aperture is provided to receive a complementary shaped end of an instrument.

15. The method of claim 1, wherein the angle is a predetermined angle that determines the angle for joint fusion.

16. The method of claim 1, wherein the angle is an obtuse angle.

17. A method for fusing the metacarpophalangeal joint, comprising:
   providing a fixation assembly, wherein the fixation assembly comprises:
      a metacarpal implant member comprising a first elongated body extending along a first longitudinal axis and a bore extending through the first elongated body along a bore axis;
      a phalangeal implant member comprising a head portion and a second elongated body extending along a second longitudinal axis; and
   forming a first bore hole in a metacarpal medullary canal;
   inserting the metacarpal implant member into the first bore hole;
   connecting the metacarpal implant member to a metacarpal bone;

forming a second bore hole in a phalangeal medullary canal;

inserting the phalangeal implant member into the metacarpal implant member;

inserting the phalangeal implant member into the second bore hole;

connecting the phalangeal implant member to a phalange bone;

applying compression to the phalangeal implant member to provide an interference fit between the metacarpal implant member and the phalangeal implant member, thereby fusing the metacarpophalangeal joint.

18. A method for fusing the metacarpophalangeal joint, comprising:
provuding a fixation assembly, wherein the fixation assembly comprises:
a metacarpal implant member comprising a first elongated body extending along a first longitudinal axis and a bore extending through the first elongated body along a bore axis;
a phalangeal implant member comprising a head portion and a second elongated body extending along a second longitudinal axis; and forming a first bore hole in a metacarpal medullary canal;

inserting the metacarpal implant member into the first bore hole;

connecting the metacarpal implant member to a metacarpal bone;

forming a second bore hole in a phalangeal medullary canal;

inserting the phalangeal implant member through the bore of the metacarpal implant member into the second bore hole;

connecting the phalangeal implant member to a phalange bone;

applying torque to the head portion of the phalangeal implant member to lock the phalangeal implant member to the metacarpal implant member, thereby compressing the phalange bone.

* * * * *